United States Patent
Takiguchi et al.

(10) Patent No.: US 9,023,330 B2
(45) Date of Patent: May 5, 2015

(54) HAIR TREATMENT COMPOSITION

(71) Applicant: Kao Corporation, Chuo-ku (JP)

(72) Inventors: Osamu Takiguchi, Sennan-gun (JP); Yuji Hirano, Chiba (JP); Mikako Ezure, Musashino (JP)

(73) Assignee: Kao Corporation, Chuo-ku (JP)

( * ) Notice: Subject to any disclaimer, the term of this patent is extended or adjusted under 35 U.S.C. 154(b) by 0 days.

(21) Appl. No.: 14/353,588

(22) PCT Filed: Nov. 28, 2012

(86) PCT No.: PCT/JP2012/080773
§ 371 (c)(1),
(2) Date: Apr. 23, 2014

(87) PCT Pub. No.: WO2013/081018
PCT Pub. Date: Jun. 6, 2013

(65) Prior Publication Data
US 2014/0290688 A1      Oct. 2, 2014

(30) Foreign Application Priority Data

Nov. 28, 2011   (JP) ................................. 2011-259448

(51) Int. Cl.
| | | |
|---|---|---|
| A61Q 5/02 | (2006.01) | |
| A61Q 5/06 | (2006.01) | |
| A61Q 5/12 | (2006.01) | |
| A61K 8/86 | (2006.01) | |
| A61K 8/37 | (2006.01) | |
| A61K 8/39 | (2006.01) | |
| A61K 8/41 | (2006.01) | |
| A45D 7/06 | (2006.01) | |
| A61K 8/34 | (2006.01) | |
| A45D 7/00 | (2006.01) | |

(52) U.S. Cl.
CPC ... *A61K 8/86* (2013.01); *A61Q 5/12* (2013.01); *A61K 8/375* (2013.01); *A61K 8/39* (2013.01); *A61K 8/416* (2013.01); *A45D 7/06* (2013.01); *A61Q 5/06* (2013.01); *A61K 8/34* (2013.01); *A61K 8/345* (2013.01); *A61K 2800/805* (2013.01); *A45D 2007/002* (2013.01)

(58) Field of Classification Search
None
See application file for complete search history.

(56) References Cited

U.S. PATENT DOCUMENTS

| | | | |
|---|---|---|---|
| 2003/0147824 A1* | 8/2003 | Terazaki et al. ............. | 424/70.2 |
| 2004/0151685 A1 | 8/2004 | Popescu et al. | |
| 2006/0198807 A1 | 9/2006 | Morioka | |
| 2007/0166272 A1 | 7/2007 | Kaharu | |
| 2008/0019937 A1 | 1/2008 | Popescu et al. | |
| 2008/0145350 A1 | 6/2008 | Popescu et al. | |
| 2009/0126754 A1 | 5/2009 | Popescu et al. | |
| 2013/0164242 A1 | 6/2013 | Tamareselvy et al. | |

FOREIGN PATENT DOCUMENTS

| | | |
|---|---|---|
| CN | 100998548 A | 7/2007 |
| EP | 0 242 792 | 10/1987 |
| EP | 1 649 847 A1 | 4/2006 |
| EP | 1 808 157 A1 | 7/2007 |
| JP | 61-259751 | 11/1986 |
| JP | 62-255408 | 11/1987 |
| JP | 2001-97825 | 4/2001 |
| JP | 2001-192324 | 7/2001 |
| JP | 2001-261530 | 9/2001 |
| JP | 2002-370943 | 12/2002 |
| JP | 2003-286139 | 10/2003 |
| JP | 2004-155699 | 6/2004 |
| JP | 2005-2038 | 1/2005 |
| JP | 2007-131581 | 5/2007 |
| JP | 2009-108085 | 5/2009 |
| WO | WO 2008/087766 A1 | 7/2008 |
| WO | WO 2012/031113 A2 | 3/2012 |
| WO | WO 2012/031113 A3 | 3/2012 |

OTHER PUBLICATIONS

JP 2004323492 , abstract (Nov. 18, 2004).*
U.S. Appl. No. 14/353,664, filed Apr. 23, 2014, Takiguchi, et al.
English translation of the International Preliminary Report on Patentability issued Jun. 12, 2014 in PCT/JP2012/080773.
English translation of the Written Opinion issued Feb. 19, 2013 in PCT/JP2012/080773.
Extended Search Report issued Aug. 5, 2014 in European Patent Application No. 12853259.5.
International Search Report issued Feb. 19, 2013, in PCT/JP12/080773 filed Nov. 28, 2012.

* cited by examiner

*Primary Examiner* — Jyothsna Venkat
(74) *Attorney, Agent, or Firm* — Oblon, McClelland, Maier & Neustadt, L.L.P.

(57) ABSTRACT

A hair treatment composition comprising components (A) to (D), wherein the mass ratio (A)/(B) between the content of the component (A) and the content of the component (B) is from 0.05 to 2.0, and the pH value of the hair treatment composition is from 2.5 to 5.0;

(A): polyglycerin, in which with regard to the ratio among a total content (p) of triglycerin and tetraglycerin, a content (q) of diglycerin, and a total content (r) of pentaglycerin and higher order oligomers in the entire polyglycerin, q/p is less than 0.5 and r/p is less than 0.5;

(B): alkyl glyceryl ester or alkyl glyceryl ether having an HLB of 2 to 7;

(C): aromatic alcohol; and (D): cationic surfactant.

12 Claims, No Drawings

HAIR TREATMENT COMPOSITION

CROSS REFERENCE TO RELATED APPLICATION

This application is a 371 of PCT/JP2012/080773, filed on Nov. 28, 2012, and claims priority to Japanese Patent Application No. 2011-259448, filed on Nov. 28, 2011.

FIELD OF THE INVENTION

The present invention relates to a hair treatment composition, which reforms the inside of hair and improves hair styling properties.

BACKGROUND OF THE INVENTION

Methods for imparting a desired style to hair and retaining it can be broadly classified into: a surface reformation method comprising allowing a hair styling component to remain on the surface of hair; and an internal reformation method comprising penetrating a hair styling component into the inside of hair. The former method is characterized in that it easily provides high hair styling properties, but it tends to provide unnatural hand feeling. On the other hand, the latter method is characterized in that it hardly provides sufficient hair styling properties, but it tends to provide natural hand feeling.

As a result of the recent trend in hairstyle, preference for natural hairstyle that is not too elaborated and good hand feeling has increased. In such background, it has been desired to develop a technique of reforming the inside of hair that provides higher hair styling effects, while keeping natural hand feeling and/or finishing.

As a technique of improving hair styling properties by reforming the inside of hair, a technique of reforming the inside of hair by allowing sugar, amino acid, enzyme or the like to penetrate into hair has been known (Patent Literatures 1 and 2). Also, it has been reported that polyglycerin having a specific molecular weight or a specific polymerization degree has excellent hair styling properties, although it has not been suggested that such polyglycerin has an internal reforming effect (Patent Literatures 3 and 4).

Moreover, in recent years, there has been a trend in which hair color is changed by a color-treatment for fashion, or hair style is changed by an entire or partial perm treatment. As a result, hair is largely damaged by such chemical treatments or daily hair washing. Under such circumstances, a hair styling agent, in which a conditioning component is combined with a glycerin derivative, has been proposed (Patent Literature 5).

CITATION LIST

Patent Literature

[Patent Literature 1] JP-A-2007-131581
[Patent Literature 2] JP-A-2009-108085
[Patent Literature 3] JP-A-2001-97825
[Patent Literature 4] JP-A-2003-286139
[Patent Literature 5] JP-A-2005-2038

SUMMARY OF THE INVENTION

The present invention provides a hair treatment composition comprising components (A) to (D), wherein the mass ratio (A)/(B) between the content of the component (A) and the content of the component (B) is from 0.05 to 2.0, and the pH value of hair treatment composition is from 2.5 to 5.0;

(A): polyglycerin, in which with regard to the ratio among a total content (p) of triglycerin and tetraglycerin, a content (q) of diglycerin, and a total content (r) of pentaglycerin and higher order oligomers in the entire polyglycerin, q/p is less than 0.5 and r/p is less than 0.5;

(B): alkyl glyceryl ester or alkyl glyceryl ether having an HLB of 2 to 7;

(C): aromatic alcohol; and (D): cationic surfactant.

The present invention also provides a hair styling method, which comprises applying the aforementioned hair treatment composition to hair, rinsing it from the hair, and then styling the hair, while blow-drying it with hot air from a dryer.

EMBODIMENTS FOR CARRYING OUT THE INVENTION

At the conventional technical level, a technique of reforming the inside of hair, which is capable of improving hair styling properties to the adequate level while keeping natural hand feeling, has not yet been discovered. In particular, when polyglycerin known to have an excellent hair styling properties is used in combination with a cationic surfactant used as a conditioning component, its hair styling properties is impaired, and when such polyglycerin is used in a large amount in order to retain such hair styling properties, stickiness is generated. Thus, polyglycerin has a trade-off problem. The present inventors have used polyglycerin, the polymerization degree distribution of which is regulated in a certain range, in combination with a cationic surfactant and a specific nonionic surfactant, and the inventors have found that both hair styling properties and good feeling can be achieved, while suppressing the amount of polyglycerin mixed.

[(A): Polyglycerin]

Polyglycerin is generally produced and sold in the form of a mixture of polymers ranging from dimers to nonamers. The present inventors have found that while trimers (triglycerin) and tetramers (tetraglycerin) contained in polyglycerin have an excellent internal reforming effect, polymers such as dimers (diglycerin), pentamers, and higher order oligomers (pentaglycerin, heptaglycerin, etc) do not have such an internal reforming effect. Moreover, the inventors have found that diglycerin with a low molecular weight easily penetrates into hair to occupies a site in which triglycerin or tetraglycerin could exhibit effects, and that diglycerin thus becomes an inhibitory factor which inhibits the achievement of an internal reforming effect. The inventors have also found that polymers with a high molecular weight, such as pentaglycerin or heptaglycerin, hardly penetrate into hair, and that thus it remains on the surface and causes a reduction in good feeling. Hence, the conventionally used polyglycerin comprises large quantities of dimers, pentamers and higher order oligomers, and as a result, sufficient hair styling effects cannot be obtained.

Herein, the term "diglycerin" is used to mean a dimer in which two molecules of glycerins bind to each other in a linear or cyclic form as a result of dehydration synthesis. The diglycerin has, for example, the form of the following compounds (2-1) or (2-2):

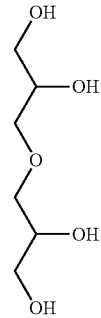

Compound (2-1)

Compound (2-2)

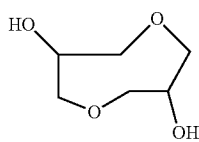

The term "triglycerin" is used herein to mean a trimer in which three molecules of glycerins bind to one another in a linear, cyclic or branched form as a result of dehydration synthesis. The triglycerin has, for example, the form of the following compounds (3-1) to (3-5):

Compound (3-1)

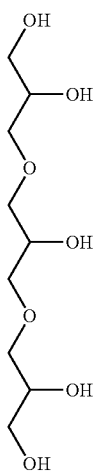

Compound (3-2)

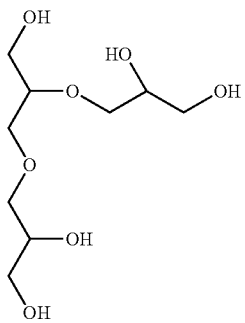

Compound (3-3)

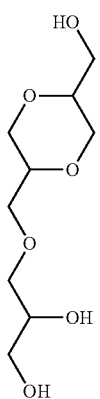

Compound (3-4)

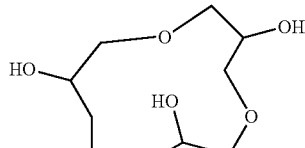

Compound (3-5)

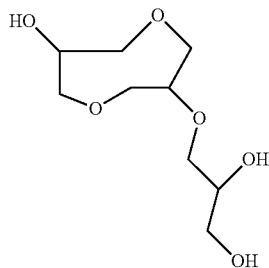

The term "tetraglycerin" is used herein to mean a tetramer in which four molecules of glycerins bind to one another in a linear, cyclic or branched form as a result of dehydration synthesis. The tetraglycerin has, for example, the form of the following compounds (4-1) to (4-9):

Compound (4-1)

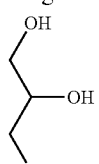

Compound (4-2)

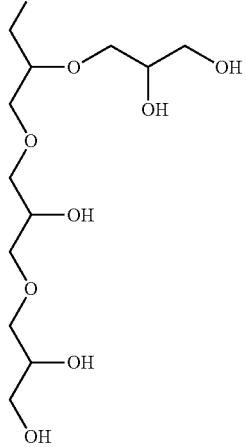

Compound (4-3)
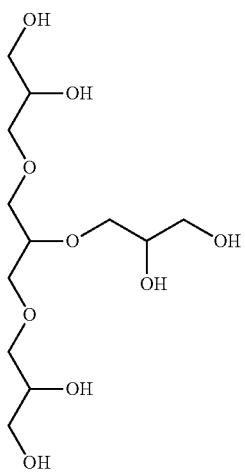
Compound (4-6)
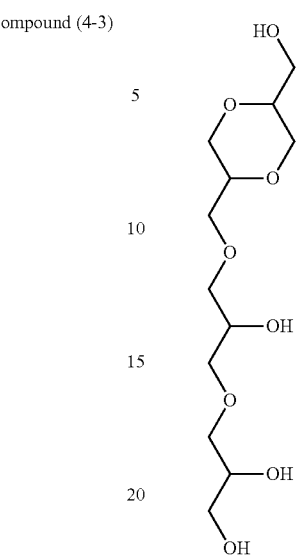
Compound (4-4)
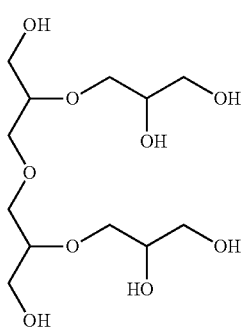
Compound (4-7)
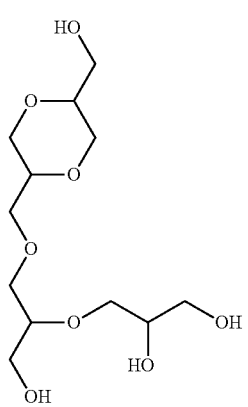
Compound (4-5)
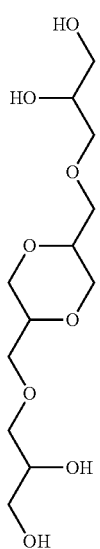
Compound (4-8)
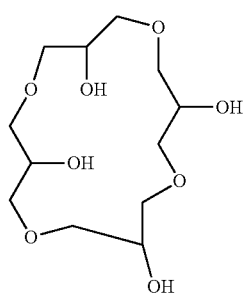
Compound (4-9)
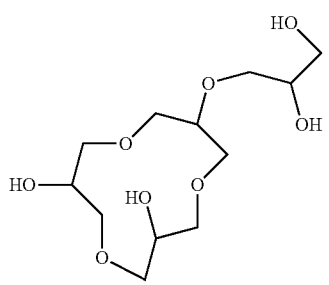
From the viewpoint of the achievement of excellent hair styling properties, with regard to polyglycerin as component (A), the ratio q/p of the content (q) of dimers to the total content (p) of trimers and tetramers in the entire polyglycerin is set at less than 0.5, preferably less than 0.4, and more preferably less than 0.3. On the other hand, from the viewpoint of feeling obtained after polyglycerin has been applied to hair, the ratio r/p of the total content (r) of pentamer and higher order oligomers to the total content (p) of trimers and tetramers in the entire polyglycerin is set at less than 0.5, preferably less than 0.4, and more preferably less than 0.2. Polyglycerin having such polymerization degree distribution has a hydroxyl value of approximately 970 to 1242 (mgKOH/g), and preferably 1000 to 1200 (mgKOH/g). Furthermore, the above described polyglycerin has a specific gravity at 30° C. of 1.271 to 1.350, and preferably 1.275 to 1.320. These physical values may be used as grounds for selecting component (A).

As such polyglycerin, two or more polyglycerins may be used in combination. In such a case, the entire polyglycerin as component (A) is required to fulfill the above described conditions. Examples of a commercially available polyglycerin that fulfills the above described conditions include polyglylcerol-3 (q/p=0.44, r/p=0.13, hydroxyl value: 1140, specific gravity: 1.285) and polyglylcerol-4 (q/p=0.03, r/p=0.37, hydroxyl value: 1053, specific gravity: 1.296), both of which are manufactured by Solvay.

The mass ratio among individual components in polyglycerin can be obtained by the following method. Specifically, trimethylsilylation is performed on a polyglycerin mixture as a measurement target so as to convert it to a polyglycerin derivative, and thereafter, the polyglycerin derivative is subjected to separation and quantification according to a GC method (gas chromatography), and the mass ratio can be then determined according to an area method. The analysis according to the GC method can be easily carried out by analyzing temperature rising from 100° C. to 320° C. at a rate of 10° C./min, using a fused silica capillary tube, to which a low-polarity liquid phase such as methyl silicone has been allowed to chemically bind. In addition, the hydroxyl value can be determined, for example, according to the method described in JIS K 1557-1. Specific gravity can be determined according to First Method A described in Japanese Standards of Quasi-drug Ingredients 2006.

The value (p) in polyglycerin as component (A) in the composition of the present invention is preferably from 52% to 100% by mass, and more preferably from 55% to 100% by mass, from the viewpoint of suppressing stickiness, while keeping excellent hair styling effects by hair internal reforming.

The content of polyglycerin as component (A) in the composition of the present invention is preferably from 0.05% to 10% by mass, more preferably from 0.075% to 5% by mass, and even more preferably from 0.1% to 2.5% by mass, from the viewpoint of suppressing stickiness, while keeping excellent hair styling effects caused by hair internal reforming.

[(B): Alkyl Glyceryl Ester or Alkyl Glyceryl Ether]

Alkyl glyceryl ester or alkyl glyceryl ether as component (B), which has an HLB of 2 to 7, creates an emulsified state with a cationic surfactant as component (D) to suppress inhibition of hair styling properties provided to the component (A). In order to create a good emulsified state, the alkyl glyceryl ester or alkyl glyceryl ether needs to be soluble in oil, and also, it preferably has an HLB of 2 to 7. Examples of such alkyl glyceryl ester or alkyl glyceryl ether include alkyl glyceryl ester and/or alkyl glyceryl ether having a linear or branched alkyl group containing 8 to 18 carbon atoms. Specific examples of such alkyl glyceryl ester or alkyl glyceryl ether include stearyl glyceryl ester, cetyl glyceryl ester, dodecyl glyceryl ester, isostearyl glyceryl ether, stearyl glyceryl ether, isodecyl glyceryl ether, 2-ethylhexyl glyceryl ether, and cetyl glyceryl ether. Among these, stearyl glyceryl ester, isostearyl glyceryl ether, stearyl glyceryl ether, and 2-ethylhexyl glyceryl ether are preferable. These substances can be used singly or in combination of two or more substances. It is to be noted that the term "HLB" is used herein to mean a value determined according to a Davis method.

It is also to be noted that alkyl glyceryl ester is generally referred to as "glyceryl alkanoate."

From the viewpoint of enhancing improvement effect of hair styling properties without impairing the feeling of the treated hair, the total content of alkyl glyceryl ester and alkyl glyceryl ether used as component (B) in the composition of the present invention is preferably 0.3% to 5.0% by mass, more preferably 0.4% to 3.0% by mass, and even more preferably 0.5% to 2.0% by mass.

Moreover, from the viewpoint of providing excellent hair styling effects by hair internal reforming, the mass ratio (A)/(B) between the content of the component (A) and the content of the component (B) is preferably from 0.05 to 2.0, more preferably from 0.07 to 1.8, and even more preferably 0.1 to 1.5.

Furthermore, from the viewpoint of providing excellent hair styling effects by hair internal reforming, the mass ratio p/(B) between the total content (p) of trimers and tetramers as portions in the component (A) and the content of the component (B) is preferably from 0.025 to 2.0, more preferably from 0.035 to 1.8, and even more preferably from 0.05 to 1.5.

[(C): Aromatic Alcohol]

Aromatic alcohol as component (C) is used from the viewpoint of promoting permeation of the polyglycerin used as a component (A) that is an internal reforming component into hair. Examples of such aromatic alcohol include benzyl alcohol, phenoxyethanol, and 2-benzyloxyethanol. These substances can be used singly or in combination of two or more substances.

The content of the aromatic alcohol used as a component (C) in the composition of the present invention is preferably from 0.05% to 7.0% by mass, more preferably from 0.1% to 5.0% by mass, and even more preferably from 0.2% to 3.0% by mass.

[(D): Cationic Surfactant]

Cationic surfactant as component (D) is adsorbed on the surface of damaged hair to suppress tangles of hair, and acts as a conditioning component. In addition, when the composition of the present invention is in the form of an emulsified cosmetic, the cationic surfactant also acts as an emulsifier.

As such a cationic surfactant, at least one or more selected from the group consisting of etheramine represented by the following general formula (1), quaternary ammonium salts represented by the following general formula (2), and amideamine represented by the following general formula (3) can be used.

In the general formula (1), $R^1$ represents a linear or branched alkyl group or alkenyl group containing 6 to 24 carbon atoms; and $R^2$ and $R^3$ are the same or different, $R^2$ and $R^3$ each represents an alkyl group containing 1 to 6 carbon atoms or the group -(AO)$_m$H (wherein A represents an alkylene group containing 2 to 4 carbon atoms, m represents a number of 1 to 6, and each of $(A)_m$ is identical to or different from one another and has any arbitrary sequence).

Specific examples of preferred etheramine include N,N-dimethyl-3-hexadecyloxypropylamine and N,N-dimethyl-3-octadecyloxypropylamine.

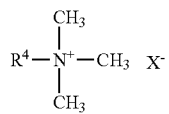
(2)

In the general formula (2), $R^4$ represents a linear or branched alkyl group or alkenyl group containing 12 to 24 carbon atoms; and $X^-$ represents an anion.

Specific examples of preferred quaternary ammonium salts include lauryl trimethyl ammonium salts, palmityl trimethyl ammonium salts, stearyl trimethyl ammonium salts, oleyl trimethyl ammonium salts, arachyl trimethyl ammonium salts, and behenyl trimethyl ammonium salts. Among these, stearyl trimethyl ammonium salts and behenyl trimethyl ammonium salts are more preferable. Examples of the anion $X^-$ include: halide ions such as chloride ions and bromide ions; and inorganic and organic anions such as methosulfate ions, ethosulfate ions, methophosphate ions, ethophosphate ions, and methocarbonate ions. Among these, halide ions, methosulfate, and ethosulfate are preferable, halide ions are more preferable, and chloride ions are even more preferable.

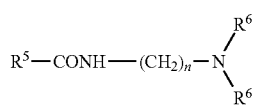
(3)

In general formula (3), $R^5$ represents a linear or branched alkyl group containing 17 to 21 carbon atoms; two $R^6$ are the same or different and each represents an alkyl group containing 1 to 4 carbon atoms; and n represents a number of 2 to 4.

Specific examples of preferred amideamine include dimethyl amino ethyl amide stearate, dimethyl amino propyl amide stearate (manufactured by TOHO Chemical Industry Co., Ltd.; Catinal MPAS), diethyl amino ethyl amide stearate (manufactured by TOHO Chemical Industry Co., Ltd.; Catinal AEAS), diethyl amino propyl amide stearate, dipropyl amino ethyl amide stearate, dipropyl amino propyl amide stearate, dimethyl amino propyl amide behenate (manufactured by Nikko Chemicals Co., Ltd.; amideamine MPB), and diethyl amino propyl amide behenate (manufactured by TOHO Chemical Industry Co., Ltd.; Catinal GMPA). Among these, dimethyl amino propyl amide stearate, diethyl amino ethyl amide stearate, dimethyl amino propyl amide behenate, diethyl amino propyl amide behenate, and the like are more preferable.

These cationic surfactants can be used singly or in combination of two or more surfactants. Among these cationic surfactants, etheramine and/or quaternary ammonium salts are preferably used in terms of feeling obtained upon application and after drying.

The content of the cationic surfactant used as component (D) in the composition of the present invention is preferably from 0.05% to 15% by mass, more preferably from 0.1% to 10% by mass, and even more preferably from 0.3% to 5% by mass, in terms of feeling obtained upon rinsing and drying and the stability of an emulsified system. When the etheramine represented by the general formula (1) or the amideamine represented by the general formula (3), which is a tertiary amine, is used as a cationic surfactant that is the component (D), it may be directly mixed into the composition without being neutralized, or may also be mixed therein after being neutralized with the after-mentioned acid.

The mass ratio (B)/(D) between the cationic surfactant used as component (D) and the component (B) in the composition of the present invention is preferably from 0.05 to 10, and more preferably from 0.1 to 5, in terms of feeling obtained upon rinsing and drying and the stability of an emulsified system.

[Higher Alcohol]

From the viewpoint of the improvement of feeling and stability, the hair treatment composition of the present invention preferably comprises higher alcohol. Such higher alcohol has the effect of improving feeling obtained upon rinsing, as well as the effect of forming a structure with a surfactant so as to prevent separation.

As such higher alcohol, higher alcohol containing preferably 8 to 22 carbon atoms, and more preferably 16 to 22 carbon atoms is used. Specific examples include cetyl alcohol, stearyl alcohol, behenyl alcohol, and a mixture thereof.

The content of the higher alcohol in the composition of the present invention is preferably from 0.01% to 20% by mass, and more preferably from 0.1% to 10% by mass.

[Cationic Polymer]

Moreover, from the viewpoint of the improvement of smoothness upon application of the composition to hair and upon drying of the hair, the hair treatment composition of the present invention may further comprise a cationic polymer. Examples of such a cationic polymer include a cationized cellulose derivative, cationic starch, a cationized guar gum derivative, a homopolymer of diallyl quaternary ammonium salts, a diallyl quaternary ammonium salt/acylamide copolymer, a quaternized polyvinylpyrrolidone derivative, a polyglycol polyamine condensate, a vinyl imidazolium trichloride/vinylpyrrolidone copolymer, a hydroxyethylcellulose/dimethyl diallyl ammonium chloride copolymer, a vinylpyrrolidone/quaternized dimethylaminoethyl methacrylate copolymer, a polyvinylpyrrolidone/alkylamino acrylate copolymer, a polyvinylpyrrolidone/alkylamino acrylate/vinyl caprolactam copolymer, a vinylpyrrolidone/methacrylamide propyl trimethylammonium chloride copolymer, an alkyl acrylamide/acrylate/alkylaminoalkyl acrylamide/polyethylene glycol methacrylate copolymer, an adipic acid/dimethylaminohydroxypropyl ethylene triamine copolymer (Cartaretin, manufactured by Sandoz Ltd., U.S.A.), and cationic polymers described in JP-A-53-139734 and JP-A-60-36407. Among these, a cationized cellulose derivative, a cationized guar gum derivative, and a diallyl quaternary ammonium salt/acrylamide copolymer are preferable. These substances can be used singly or in combination of two or more substances.

The content of the cationic polymer in the composition of the present invention is preferably from 0.02% to 5% by mass, more preferably from 0.05% to 1% by mass, and even more preferably from 0.1% to 0.7% by mass, in terms of the improvement of the manageability of hair after drying and feeling after drying.

[Silicone]

Furthermore, in terms of smoothness upon application to hair and upon drying of the hair, the hair treatment composition of the present invention may further comprise silicone. Examples of such silicone are as follows.

(1) Dimethyl Polysiloxane

Dimethyl polysiloxane represented by the following general formula may be used, for example:

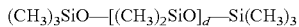
$(CH_3)_3SiO-[(CH_3)_2SiO]_d-Si(CH_3)_3$ wherein d represents a number of 3 to 20000.

(2) Amino-Modified Silicone

Various types of amino-modified silicones can be used. Among these, amino-modified silicone having a mean molecular weight of approximately 3,000 to 100,000, which is described with the name "Amodimethicone" in the $3^{rd}$ edition of CTFA Dictionary (Cosmetic Ingredient Dictionary, U.S.A.), is preferable. This amino-modified silicone is preferably used in the form of an aqueous emulsion, and commercially available products of this amino-modified silicone include SM 8704C (Dow Corning Toray Co., Ltd.), DC 929 (Dow Corning), and KT 1989 (Momentive Performance Materials, Inc.).

(3) Other Silicones

In addition to the above-mentioned silicones, examples of other silicones include polyether-modified silicone, methylphenyl polysiloxane, fatty acid-modified silicone, alcohol-modified silicone, alkoxy-modified silicone, epoxy-modified silicone, fluorine-modified silicone, cyclic silicone, and alkyl-modified silicone. These substances can be used singly or in combination of two or more substances.

The content of the silicone in the composition of the present invention is preferably from 0.01% to 10% by mass, more preferably from 0.05% to 6% by mass, and even more preferably from 0.3% to 3% by mass, in terms of smoothness from application to hair until rinsing the hair.

[Oil Agent]

Further, the hair treatment composition of the present invention may also comprise an oil agent as another conditioning agent. Examples of such an oil agent include: hydrocarbons such as squalene, squalane, liquid paraffin, liquid isoparaffin and cycloparaffin; glycerides such as castor oil, cacao oil, mink oil, avocado oil and olive oil; waxes such as beeswax, spermaceti, lanolin and carnauba wax; polyhydric alcohols such as glycerin; esters such as isopropyl palmitate, isopropyl myristate, octyl dodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearyl acid, and isopalmitic acid; and polyoxy propylene butyl ether. These oil agents may also be used in combination of two or more oil agents. The content of the oil agent in the hair treatment composition of the present invention is preferably from 0.2% to 2% by mass, more preferably from 0.3% to 1.8% by mass, and even more preferably from 0.5% to 1.5% by mass.

[Medium]

In the hair treatment composition of the present invention, water and, as necessary, an organic solvent other than the component (C) are used as media. Examples of such an organic solvent include: lower alkanols such as ethanol and 2-propanol; polyols such as propylene glycol, 1,3-butanediol, diethylene glycol and glycerin; cellosolves such as ethyl cellosolve and butyl cellosolve; and carbitols such as ethyl carbitol and butyl carbitol.

The content of water in the hair treatment composition of the present invention is preferably 50% by mass or more, more preferably from 60% to 97% by mass, and even more preferably from 70% to 95% by mass.

[Other Components]

In addition to the above-mentioned components, the hair treatment composition of the present invention may also comprise other components generally used as raw materials for cosmetics. Examples of such components include antiseptics, chelating agents, stabilizers, antioxidants, plant extracts, herbal extracts, protein hydrolysates, vitamins, coloring agents such as dyes, perfumes, ultraviolet absorbers, pearling agents such as ethylene glycol difatty acid ester, polymers for hair setting, and amphiphilic amide lipids.

[pH]

From the viewpoint of promoting permeation of polyglycerin as component (A) that is an internal reforming component into the inside of hair, the pH value of the hair treatment composition of the present invention at 25° C. is preferably from 2.5 to 5.0, and more preferably from 3.0 to 4.5.

In order to adjust the pH value of the hair treatment composition of the present invention within the aforementioned range, it is preferable to use organic acid, and it is more preferable to use hydroxycarboxylic acid. Specific examples of such hydroxycarboxylic acid include glycolic acid, lactic acid, malic acid, tartaric acid, citric acid, gluconic acid, and pantothenic acid. The amount of the organic acid used is arbitrarily determined, such that the pH value of the hair treatment composition of the present invention can be set within the aforementioned range.

[Form of Composition]

The hair treatment composition of the present invention can be processed into any form, as long as it is a form applicable to hair. Specific examples of such a form include hair shampoo, hair rinse, hair conditioner, hair styling, and hair dye. The present hair treatment composition, which can be processed into the aforementioned forms, can take various formulations such as liquid, cream, gel, mist, foam, and spray.

[Method for Treating Hair]

In order to remove from hair unnecessary components remaining on the hair, which do not contribute to hair styling properties, and to achieve the natural feeling of the hair, the hair treatment composition of the present invention is preferably rinsed from hair, after it has been applied to the hair. Thereafter, the hair can be treated by drying. In addition, this drying may be natural drying, but in order to impart sufficient hair styling properties to hair, it is preferable to style hair while drying the hair with hot air from a dryer. By this treatment, hair can be preferably styled.

[Method for Re-Styling Hair]

The hair treatment composition of the present invention can be used for re-styling, after completion of the above described hair treatment, which comprises applying the hair treatment composition to hair, rinsing it from the hair, and then drying the hair. That is to say, after the hair has been dried by natural drying or with hot hair from a dryer, the hair can be styled, immediately or after a certain time period, such as after leaving overnight. When hair is re-styled, water, a solvent or the like may be first put on the hair to get it wet, and the hair may be then re-styled. In the present invention, however, it is not always necessary to get hair wet. Then, hair can be styled by heating the hair using a heat generation type hair styling device such as a dryer, a hot curler, electric hair tongs or an iron.

With regard to the above-mentioned embodiments, preferred aspects of the present invention will be further disclosed below.

<1>

A hair treatment composition comprising components (A) to (D), wherein the mass ratio (A)/(B) between the content of the component (A) and the content of the component (B) is from 0.05 to 2.0, and the pH value of the hair treatment composition is from 2.5 to 5.0;

(A): polyglycerin, in which with regard to the ratio among a total content (p) of triglycerin and tetraglycerin, a content (q) of diglycerin, and a total content (r) of pentaglycerin and higher order oligomers in the entire polyglycerin, q/p is less than 0.5 and r/p is less than 0.5;

(B): alkyl glyceryl ester or alkyl glyceryl ether having an HLB of 2 to 7;

(C): aromatic alcohol; and (D): cationic surfactant.

<2>

The hair treatment composition according to <1> above, wherein the content of the component (A) is preferably from 0.05% to 10% by mass, more preferably from 0.075% to 5% by mass, and even more preferably from 0.1% to 2.5% by mass.

<3>

The hair treatment composition according to <1> or <2> above, wherein q/p in the component (A) is preferably less than 0.4, and more preferably less than 0.3.

<4>

The hair treatment composition according to any one of <1> to <3> above, wherein r/p in the component (A) is preferably less than 0.4, and more preferably less than 0.2.

<5>

The hair treatment composition according to any one of <1> to <4> above, wherein the content of the component (B) is preferably from 0.3% to 5.0% by mass, more preferably from 0.4% to 3.0% by mass, and even more preferably from 0.5% to 2.0% by mass.

<6>

The hair treatment composition according to any one of <1> to <5> above, wherein the mass ratio (A)/(B) between the component (A) and component (B) is preferably from 0.05 to 2.0, more preferably from 0.07 to 1.8, and even more preferably from 0.1 to 1.5.

<7>

The hair treatment composition according to any one of <1> to <6> above, wherein the mass ratio p/(B) between the total content (p) of trimers and tetramers in the component (A) and the content of the component (B) is preferably from 0.025 to 2.0, more preferably from 0.035 to 1.8, and even more preferably from 0.05 to 1.5.

<8>

The hair treatment composition according to any one of <1> to <7> above, wherein the content of the component (C) is preferably from 0.05% to 7.0% by mass, more preferably from 0.1% to 5.0% by mass, and even more preferably from 0.2% to 3.0% by mass.

<9>

The hair treatment composition according to any one of <1> to <8> above, wherein the content of the component (D) is preferably from 0.05% to 15% by mass, more preferably from 0.1% to 10% by mass, and even more preferably from 0.3% to 5% by mass.

<10>

The hair treatment composition according to any one of <1> to <9> above, wherein the mass ratio (B)/(D) between the component (B) and the component (D) is preferably from 0.05 to 10, and more preferably from 0.1 to 5.

<11>

The hair treatment composition according to any one of <1> to <10> above, which is rinsed from hair, after it has been applied thereto.

<12>

A method for treating hair, which comprises applying the hair treatment composition according to any one of <1> to <11> above to hair, rinsing it from the hair, and then drying the hair by natural drying or by blow-drying with hot air from a dryer.

<13>

A method for styling hair, which comprises applying the hair treatment composition according to any one of <1> to <11> above to hair, rinsing it from the hair, and then styling the hair while drying it by natural drying or by blow-drying with hot air from a dryer.

<14>

A method for re-styling hair, which comprises applying the hair treatment composition according to any one of <1> to <11> above to hair, rinsing it from the hair, then drying the hair by natural drying or by blow-drying with hot air from a dryer, and then styling the hair by heating it using a heat generation type hair styling device such as a dryer, a curler, electric hair tongs or an iron.

<15>

Use of the hair treatment composition according to any one of <1> to <11> above for treating hair, which comprises applying the hair treatment composition according to any one of <1> to <11> above to hair, rinsing it from the hair, and then drying the hair by natural drying or by blow-drying with hot air from a dryer.

<16>

Use of the hair treatment composition according to any one of <1> to <11> above for styling hair, which comprises applying the hair treatment composition according to any one of <1> to <11> above to hair, rinsing it from the hair, and then styling the hair while drying it by natural drying or by blow-drying with hot air from a dryer.

<17>

Use of the hair treatment composition according to any one of <1> to <11> above for re-styling hair, which comprises applying the hair treatment composition according to any one of <1> to <11> above to hair, rinsing it from the hair, then drying the hair by natural drying or by blow-drying with hot air from a dryer, and then styling the hair by heating it using a heat generation type hair styling device such as a dryer, a curler, electric hair tongs or an iron.

EXAMPLES

Examples 1 to 6 and Comparative Examples 1 to 6

Hair conditioners shown in Table 3 were prepared, and the hair styling properties of each hair conditioner to damaged hair was then evaluated in accordance with the following methods and standards.

<Preparation of Damaged Hair>

5 g of hair tress was prepared from chemically untreated, Japanese unwanted fuzzy hair, and the following permanent treatment was performed on the hair tress once. Thereafter, a series of bleaching operations, as described below, were performed thereon five times, so as to prepare damaged hair.

Permanent treatment: Pre-Mina Wave Lotion (hard type) manufactured by Kao Professional Services Co., Ltd. was used. First, a first part was applied to the hair tress at a bath ratio of 1:1, and it was then left at a room temperature for 30 minutes, followed by rinsing it from the hair tress with running water. Subsequently, a second part was applied to the hair tress at a bath ratio of 1:1, and it was then left at a room temperature for 30 minutes, followed by rinsing it from the hair tress with running water. Upon performing these operations, in order to keep the original unruly shape, the operations were carried out such that a load was not applied on the hair tress. As a finishing operation, the hair tress was washed with a shampoo for evaluation shown in Table 1. Thereafter, it was treated with a conditioner for evaluation shown in Table 2, and the conditioner was then rinsed from the hair tress, followed by blow-drying.

Thereafter, a series of operations such as washing with the shampoo, treatment with the conditioner, and blow-drying were carried out repeatedly 15 times.

Bleaching treatment: a first part and a second part of Puritia Funwari Awa Bleach (high bleach) manufactured by Kao Corporation were mixed with each other, and the obtained mixture was applied to the hair tress at a bath ratio of 1:1. Thereafter, it was left at a room temperature for 30 minutes. After the agent was fully rinsed with running water, the hair was washed with the shampoo for evaluation shown in Table 1, and it was treated with the conditioner for evaluation shown in Table 2. Then, the conditioner was rinsed from the hair, and the resulting hair was blow-dried.

Thereafter, a series of operations such as washing with the shampoo, treatment with the conditioner, and blow-drying were carried out repeatedly 15 times.

TABLE 1

| Shampoo for evaluation | Mixed amount (% by mass) |
|---|---|
| Ion exchange water | 82.40 |
| EDTA-2Na (*1) | 0.30 |
| Na benzoate aqueous solution (35% by mass) | 1.43 |
| Lauramide DEA (*2) | 1.50 |
| Na laureth sulfate (*3) | 14.35 |
| Phosphoric acid | 0.02 |
| Total | 100.00 |

(*1) Clewat N, manufactured by Nagase ChemteX Corporation
(*2) AMINON L-02, manufactured by Kao Corporation
(*3) EMAL 227 (25% by mass aqueous solution), manufactured by Kao Corporation

TABLE 2

| Conditioner for evaluation | Mixed amount (% by mass) |
|---|---|
| Ion exchange water | 88.83 |
| Methyl p-hydroxybenzoate | 0.1 |
| Cetearyl alcohol (*4) | 2.0 |
| Propylene glycol | 5.0 |
| Distearyldimonium chloride (*5) | 2.7 |
| Isopropyl alcohol | 0.61 |
| Steartrimonium chloride (*6) | 0.76 |
| Total | 100.0 |

(*4) KALCOL 6870, manufactured by Kao Corporation
(*5) QUARTAMIN D86P (75% by mass aqueous solution), manufactured by Kao Corporation
(*6) QUARTAMIN 86W (28% by mass aqueous solution), manufactured by Kao Corporation <Measurement of Hair Styling Properties>

A portion with a length of 20 mm was cut from a portion with a curl radius of 10 mm in the damaged hair, and eight samples were prepared. Thereafter, 1.0 g of a weight was attached to a tip of each sample, and it was then immersed in ion exchange water for 30 minutes. Subsequently, a tip on a side opposite to the weight was held and drawn up, and the sample was then dried at 75° C. for 10 seconds with the weight which was still attached. The sample was left as was at 20° C. for 5 minutes. Thereafter, the weight was removed from the sample, and the curl radius r was then measured.

Subsequently, the same sample as used above was washed with the shampoo for evaluation of Table 1, and each conditioner shown in Table 3 was then applied to the sample at a bath ratio of 1:1. Then, the sample was retained at 38° C. for 30 minutes. Thereafter, the sample was rinsed with running water, and 1.0 g of a weight was linearly set in the same manner as described above. Then, the curl radius r' was measured.

Hair styling properties were defined as $[(r'/r)-1] \times 100$, and the hair styling properties was then evaluated using a mean value of the eight samples and standard deviation. The results are shown in Table 3.

The higher the hair styling properties, the more preferable it is. The smaller the standard deviation, the higher the homogeneity that can be favorably obtained.

TABLE 3

| | Example | | | | | | Comparative Example | | | | | |
|---|---|---|---|---|---|---|---|---|---|---|---|---|
| Raw material (% by mass) | 1 | 2 | 3 | 4 | 5 | 6 | 1 | 2 | 3 | 4 | 5 | 6 |
| Polyglycerin (1) (*7) | 0.25 | 0.12 | 0.25 | 0.25 | 0.125 | 1.0 | 0.25 | 0.25 | 0.25 | | 0.25 | 0.25 |
| Polyglycerin (2) (*8) | | 0.13 | | | | | | | | | | |
| Polyglycerin(3) (*9) | | | | | | | | | | 0.25 | | |
| Glyceryl stearate (*10) | 1.0 | | | 2.0 | 1.0 | 0.5 | 1.0 | 1.0 | | 1.0 | | |
| Isostearyl glyceryl ether (*11) | | 1.0 | | | | | | | | | | |
| 2-Ethylhexyl glyceryl ether (*12) | | | 1.0 | | | | | | | | | |
| Triethyl hexanoine (*13) | | | | | | | | | | | 1.0 | |
| Butyl glyceryl ether (*14) | | | | | | | | | | | | 1.0 |
| Stearoxy propyl diethyl amine solution (*15) | 1.5 | 1.5 | | 1.5 | 1.5 | 1.5 | 1.5 | | 1.5 | 1.5 | 1.5 | 1.5 |
| Steartrimonium chloride (*6) | | | 1.5 | | | | | 1.5 | | | | |
| Stearyl alcohol (*16) | 6.0 | 6.0 | 6.0 | 6.0 | 6.0 | 6.0 | 6.0 | 6.0 | 6.0 | 6.0 | 6.0 | 6.0 |
| Benzyl alcohol | 0.3 | 0.3 | 0.3 | 0.3 | 0.3 | 0.3 | 0.3 | — | 0.3 | 0.3 | 0.3 | 0.3 |
| Dipropylene glycol | 2.5 | 2.5 | 2.5 | 2.5 | 2.5 | 2.5 | 2.5 | 2.5 | 2.5 | 2.5 | 2.5 | 2.5 |
| Lactic acid | 1.6 | 1.6 | 1.6 | 1.6 | 1.6 | 1.6 | 1.6 | — | 1.6 | 1.6 | 1.6 | 1.6 |
| Phosphoric acid | | | | | | | | q.s. | | | | |
| Sodium hydroxide aqueous solution | | | | | | | | q.s. | | | | |
| Ion exchange water | Balance | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 | 100 |
| Mass ratio (A)/(B) | 0.25 | 0.25 | 0.25 | 0.125 | 0.125 | 2.0 | 0.25 | 0.25 | — | 0.25 | 0.25 | 0.25 |
| pH (25° C.) | 3.3 | 3.3 | 3.3 | 3.3 | 3.9 | 3.9 | 6.8 | 3.3 | 3.3 | 3.3 | 3.3 | 3.3 |

TABLE 3-continued

| Raw material (% by mass) | Example | | | | | | Comparative Example | | | | | |
|---|---|---|---|---|---|---|---|---|---|---|---|---|
| | 1 | 2 | 3 | 4 | 5 | 6 | 1 | 2 | 3 | 4 | 5 | 6 |
| Hair styling properties (mean value) | 23.9 | 30.2 | 20.6 | 23.9 | 20.3 | 17.9 | 7.1 | 0.0 | 2.5 | 7.7 | 6.9 | 0.0 |
| Standard deviation of hair styling properties (n = 8) | 12.3 | 16.5 | 11.0 | 12.3 | 8.9 | 9.6 | 6.3 | 4.6 | 14.0 | — | — | — |

(*7) Polyglycerol-3, manufactured by Solvay (q/p = 0.44, r/p = 0.13, hydroxyl value: 1140, specific gravity: 1.285)
(*8) Polyglycerol-4, manufactured by Solvay (q/p = 0.03, r/p = 0.37, hydroxyl value: 1053, specific gravity: 1.296)
(*9) Polyglycerin #750, manufactured by Sakamoto Yakuhin Kogyo Co., Ltd. (q/p = 0.61, r/p = 1.22, hydroxyl value: 890, specific gravity: 1.2633)
(*10) RHEODOL MS60, manufactured by Kao Corporation (HLB: 3.5)
(*11) PENETOL GE-IS, manufactured by Kao Corporation (HLB: 2.1)
(*12) PENETOL GE-EH, manufactured by Kao Corporation (HLB: 6.9)
(*13) EXCEPAL TGO, manufactured by Kao Corporation (HLB: 1.4), alias: triglyceride 2-ethylhexanoate
(*14) purchased as a reagent from Aldrich (HLB: 8.8)
(*15) FARMIN DM E-80, manufactured by Kao Corporation (90% by mass)
(*16) KALCOL 8098, manufactured by Kao Corporation As shown in Table 3, high hair styling properties could be obtained even in the coexistence of a cationic surfactant by using polyglycerin having a specific polymerization degree distribution in combination with alkyl glyceryl ester or alkyl glyceryl ether having an HLB of 2 to 7.

Moreover, when the hair treatment composition of the present invention is used for hair, natural hand feeling can be provided from the hair.

Example 7 and Comparative Example 7

Hair conditioners shown in Table 4 were prepared.

3 g of hair tress was prepared from chemically untreated, Japanese unwanted fuzzy hair, and the above described damaging treatment was carried out thereon.

Thereafter, the resulting hair tress was washed with the shampoo for evaluation shown in Table 1, and the hair conditioner shown in Table 4 was applied at a bath ratio of 1:0.2 to the hair. One minute later, the hair conditioner was rinsed from the hair with running water. After the hair had been towel-dried, it was blow-dried. Subsequently, in order to homogenize the surface condition for the purpose of evaluating an internal reforming effect, the hair was washed with the shampoo for evaluation shown in Table 1, was then treated with the conditioner for evaluation shown in Table 2, and was then blow-dried. The aforementioned series of hair treatments were carried out repeatedly 7 times, after completion of the damaging treatment operations. Upon the final blow-drying, blowing was carried out with fingers, while trying to style the hair tress by hand combing.

<Evaluation of Manageability/Feeling>

The manageability of each hair tress treated with a hair conditioner was visually observed, and it was then scored in accordance with the following standards. An average score of five evaluators was defined as a score for evaluation of styling ease.

3: Both the intermediate portion and the tip of the hair tress are well styled, with no floating hair.

2: The intermediate portion of the hair tress is well styled, but there is a little floating hair and the hair tip comes loose.

1. There is floating hair and the hair tress comes entirely loose.

Subsequently, fingers were passed through the hair tress. Based on the feeling of being caught in the hair tress and stiffness, the hair tress was scored in accordance with the following standards, and feeling was evaluated. An average score of five evaluators was defined as a score for evaluation of feeling.

3. There is almost no feeling of being caught in the hair tress, and natural feeling can be obtained from smooth and silky hair.

2. There is slight feeling of being caught in the hair tress, but it is close to natural feeling.

1. There is slight feeling of being caught in the hair tress, and stiffness appears at the hair tip.

TABLE 4

| Raw material (% by mass) | Example 7 | Comparative Example 7 |
|---|---|---|
| Polyglycerin (1) (*7) | 0.25 | 0.25 |
| Glyceryl stearate (*10) | 1.0 | — |
| Stearoxy propyl diethyl amine (*13) | 1.75 | 1.75 |
| Stearyl alcohol (*14) | 5.35 | 5.35 |
| Isopropyl palmitate (*17) | 0.3 | 0.3 |
| Dimethicone (*18) | 1.7 | 1.7 |
| Biscetearyl amodimethicone (*19) | 0.2 | 0.2 |
| Dipropylene glycol | 4.7 | 4.7 |
| Benzyl alcohol | 0.3 | 0.3 |
| Lactic acid | 2.0 | 2.0 |
| Purified water | Balance | Balance |
| Total | 100 | 100 |
| Mass ratio (A)/(B) | 0.25 | — |
| pH (25° C.) | 3.3 | 3.3 |
| Evaluation of manageability (mean value) | 2.8 | 1.2 |
| Evaluation of feeing (mean value) | 2.8 | 2.2 |

(*17) EXCEPAL IPP, manufactured by Kao Corporation
(*18) Silicone BY11-039, manufactured by Dow Corning Toray Co., Ltd.
(*19) Silicone XF42-C4570, manufactured by Momentive Performance Materials, Inc.

As shown in Table 4, the hair treated with the conditioner of the present invention was well styled as a result of the high hair styling properties of the conditioner (namely, good alignment of the hair) while remaining good natural feeling.

Examples 8 and 9, and Comparative Example 8

Hair conditioners shown in Table 5 were prepared, and their hair styling properties were then evaluated according to the same methods and standards as those described above (Examples 1 to 6 and Comparative Examples 1 to 6). The hair styling properties of each conditioner to the damaged hair were evaluated. However, the evaluation results of each hair styling properties in Examples 8 and 9 and Comparative Example 8 are given, not as an average of eight samples, but as evaluation results obtained from only a single sample.

TABLE 5

| Raw material (% by mass) | Example 8 | Example 9 | Comparative Example 8 |
|---|---|---|---|
| Polyglycerin (1) (*7) | 1.0 | 4.0 | 1.0 |
| Glyceryl stearate (*10) | 1.0 | 2.0 | 1.0 |
| Stearoxy propyl diethyl amine solution (*15) | 1.5 | 1.5 | 1.5 |
| Stearyl alcohol (*16) | 6.0 | 6.0 | 6.0 |
| Benzyl alcohol | 0.3 | 0.3 | 0.3 |
| Dipropylene glycol | 2.5 | 2.5 | 2.5 |
| Lactic acid | 1.6 | 1.6 | 1.6 |
| Potassium hydroxide (48% by mass) | | | q.s. |
| Ion exchange water | Balance | Balance | Balance |
| Total | 100 | 100 | 100 |
| Mass ratio (A)/(B) | 1.0 | 2.0 | 1.0 |
| pH (25° C.) | 3.3 | 3.3 | 6.8 |
| Hair styling properties (n = 1) | 25 | 27 | 7 |

The invention claimed is:

1. A hair treatment composition comprising components (A) to (D), wherein the mass ratio (A)/(B) between the content of the component (A) and the content of the component (B) is from 0.05 to 2.0, and the pH value of the hair treatment composition is from 2.5 to 5.0;
    (A): polyglycerin, wherein the polyglycerine is polyglycerol-3 or polyglycerol-4 or combinations thereof
    (B): alkyl glyceryl ester or alkyl glyceryl ether having an HLB of 2 to 7;
    (C): aromatic alcohol; and
    (D): cationic surfactant.

2. The hair treatment composition according to claim 1, wherein the content of the component (A) is from 0.05% to 10% by mass.

3. The hair treatment composition according to claim 1, wherein the content of the component (B) is from 0.3% to 5.0% by mass.

4. The hair treatment composition according to claim 1, wherein the mass ratio (A)/(B) between the component (A) and component (B) is from 0.05 to 2.0.

5. The hair treatment composition according to claim 1, wherein the content of the component (A) is from 0.05% to 10% by mass and the content of the component (B) is from 0.3% to 5.0% by mass.

6. The hair treatment composition according to claim 1, wherein the content of the component (C) is from 0.05% to 7.0% by mass.

7. The hair treatment composition according to claim 1, wherein the content of the component (D) is from 0.05% to 15% by mass.

8. The hair treatment composition according to claim 1, wherein the mass ratio between the component (B) and the component (D) is from 0.05 to 10.

9. The hair treatment composition according to claim 1, which is rinsed from hair, after it has been applied thereto.

10. A method for treating hair, which comprises applying the hair treatment composition according to claim 1 to hair, rinsing it from the hair, and then drying the hair by natural drying or by blow-drying with hot air from a dryer.

11. A method for styling hair, which comprises applying the hair treatment composition according to claim 1 to hair, rinsing it from the hair, and then styling the hair while drying it by natural drying or by blow-drying with hot air from a dryer.

12. A method for re-styling hair, which comprises applying the hair treatment composition according to claim 1 to hair, rinsing it from the hair, drying the hair by natural drying or by blow-drying with hot air from a dryer, and then styling the hair by heating it using a heat generation hair styling device.

* * * * *